United States Patent [19]
Mushabac

[11] 3,971,133
[45] July 27, 1976

[54] DENTAL RESTORATION

[76] Inventor: David R. Mushabac, 18 Graham Ave., Brooklyn, N.Y. 11206

[22] Filed: Oct. 29, 1974

[21] Appl. No.: 518,266

[52] U.S. Cl. .................................................. 32/2
[51] Int. Cl.² ..................................... A61C 13/00
[58] Field of Search ................................. 32/2, 8

[56] References Cited
UNITED STATES PATENTS
| | | | |
|---|---|---|---|
| 1,702,212 | 2/1929 | Johnson | 32/8 |
| 1,803,680 | 5/1931 | Schwartz | 32/12 |
| 3,052,982 | 9/1962 | Weinstein et al. | 32/8 |

Primary Examiner—Robert Peshock
Attorney, Agent, or Firm—McAulay, Fields, Fisher, & Goldstein

[57] ABSTRACT

A porcelain preform is ultrasonically shaped by a metal model of the prepared tooth and by a metal model of the counter, both models acting as ultrasonic drills. A wax preform having a porcelain front surface congruent to the porcelain preform is used to provide indexing of the porcelain preform.

10 Claims, 6 Drawing Figures

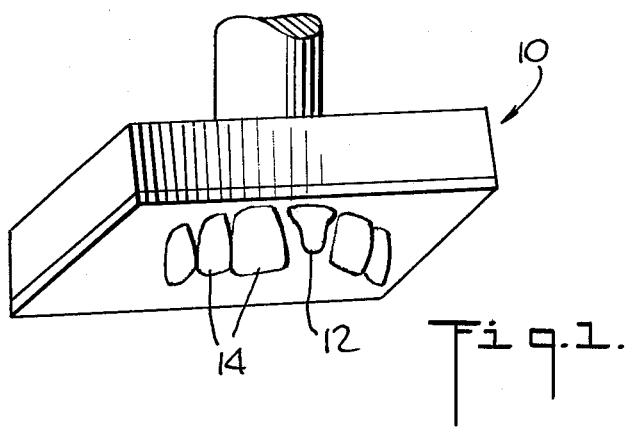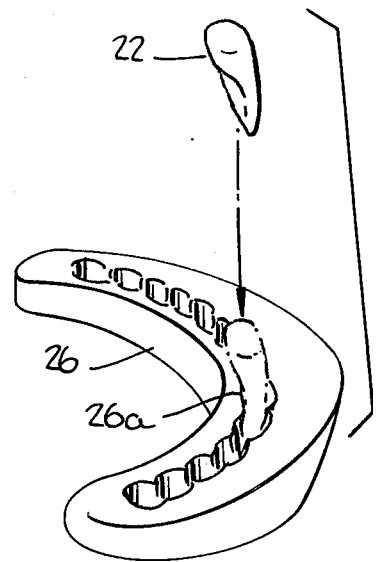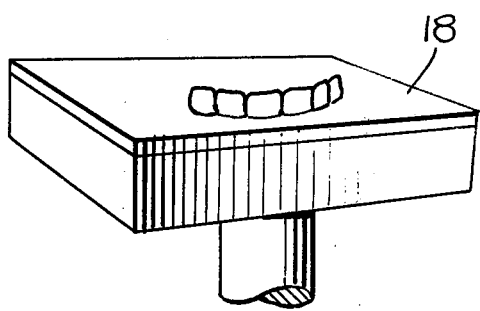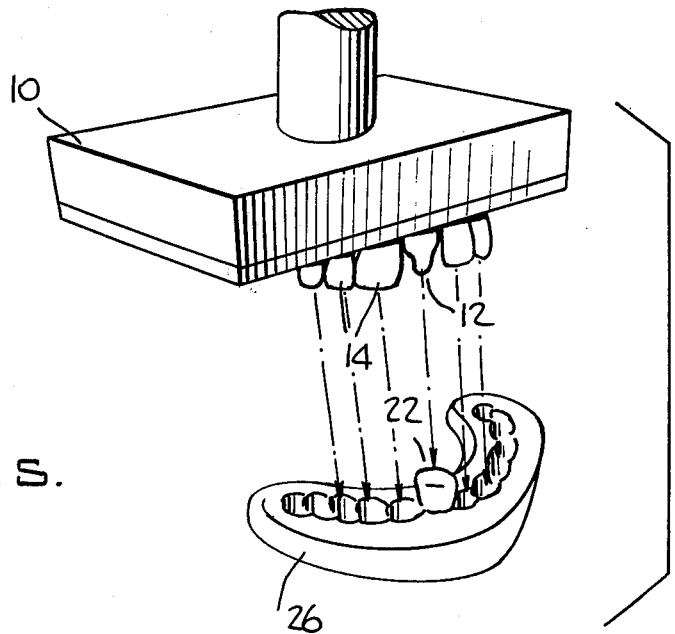

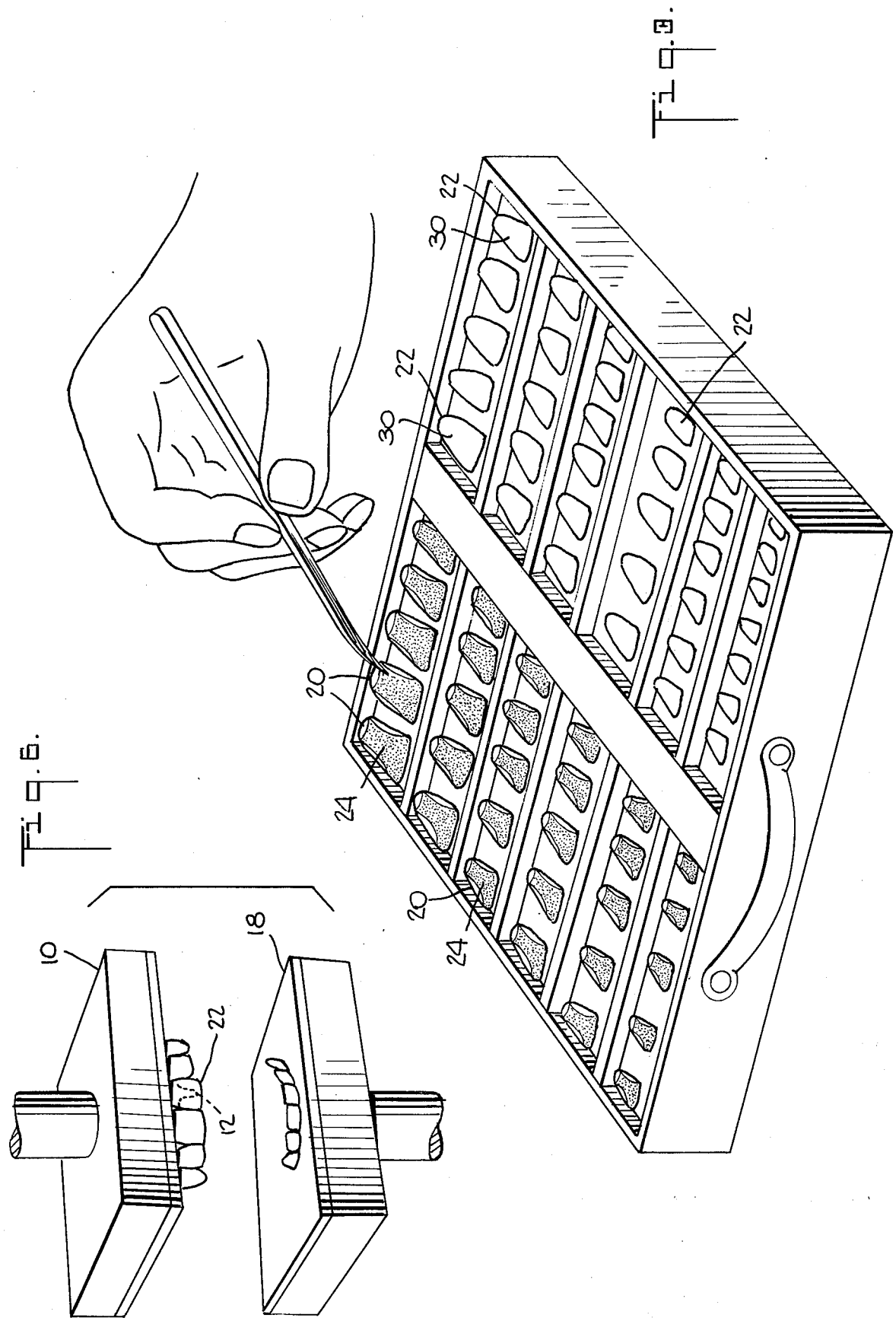

DENTAL RESTORATION

BACKGROUND OF THE INVENTION

This invention relates in general to techniques and apparatus employed in constructing the crown or bridge or other item used in dental restoration.

Known techniques of preparing and restorating crown are time consuming. Not only do they take a considerable amount of the dentist's time but a great deal of time is taken in the preparation of dies and models, articulations, and in the making of articulations, prior to the step of fabrication or cutting of the crown. More time is taken in a series of fittings to provide a crown which occludes properly with the rest of the teeth in the mouth, maintains correct margins and contacts and feels comfortable to the patient. In addition, there is usually a great deal of time between visits of the patient to the dentist during which period the patient must wear a substitute temporary crown, while the steps for making the final crown are proceeding.

Accordingly, the major purpose of this invention is to provide a much more expeditious technique for preparing the crown and restoration for the patient's tooth.

It is a related purpose of this invention to provide a technique which reduces the number of visits required.

It is another purpose of this invention to provide a technique which, in large part because of the saving of time, reduces the cost of preparing the crown.

A major time consuming problem with the known techniques of preparing and manufacturing a crown is in obtaining the desired dimensions and, more importantly, the proper occluding of the biting surfaces of the crown with the opposing teeth.

Accordingly, it is another important purpose of this invention to provide a crown forming technique that will result in an improved accurate and effective occluding, fitting of the crown with the surrounding and opposing teeth.

It is a further particular purpose of this invention to achieve this improved accuracy and improved occluding matching or fitting while at the same time obtaining the objectives fo reducing a dentist's time, reducing time lapse between visits and reducing total costs.

It is a further purpose of this invention to provide an improved method of matching the crown color and shade to the patient's teeth.

BRIEF DESCRIPTION OF THE INVENTION

One embodiment employs a positive metal model of the prepared tooth (that is, the tooth that has been cut down to the preferred form which is the anchor on which the crown is positioned) and a positive metal model of the counter (that is, a metal model of the tooth or teeth opposite from the prepared tooth). These two metal models can be prepared from a wax or alginate negative that is plated with a soft metal such as copper or nickel to provide an accurate surface and which is then filled with plastic. The removal of the wax or alginate leaves a metal plated die that constitutes the metal model.

A porcelain and wax pre-form is selected from a set of wax pre-forms on the basis of the best match to the space around the prepared tooth (that is, the tooth to be capped or crowned). This porcelain wax pre-form is inserted over the prepared tooth. A portion of the front positioned surface of the pre-form is porcelain. The pre-form is positioned to provide proper alignment of the porcelain front surface with the surrounding teeth. The wax surfaces of the pre-form are shaped to aid in this alignment. A plaster impression is then taken of the tooth having the porcelain-and-wax pre-form on it. This plaster impression, when removed from the teeth, will carry the wax pre-form with it. The wax pre-form is then removed from the plaster impression. The plaster impression thus provides a negative of the area around the prepared tooth. The wax pre-form is replaced in the impression with a solid porcelain pre-form that corresponds to the wax pre-form on the basis of both pre-forms having an identical front surface.

The positive metal model of the prepared tooth and adjacent teeth is aligned with this plaster negative model after the porcelain-wax pre-form has been removed. This alignment is fixed and repeatable by mounting the plaster impression in a nesting-fitting position with the metal positive model. The metal positive model is fixed on a vertical slide so that it can descend and mesh into the plaster negative model. (This metal positive model and plaster negative model would mesh except for the porcelain preform). The metal positive model of the prepared tooth is connected to a source of ultrasonic energy and moved into a meshing relation with the plaster negative model. This metal model acts as a cutting tool and drills into the porcelain pre-form until the metal model meshes with the rest of the plaster preform. Thus the core of the porcelain model as well as its sides are drilled and shaped.

The drilled and shaped porcelain pre-form (which now is close to its final crown shape) is placed on the metal model of the prepared tooth. The two metal models (prepared tooth and counter) are next properly aligned with one another. The counter metal model is now ultrasonically energized and used as the cutting tool as it is brought into occlusion with the metal model of the prepared and adjacent teeth. The counter shapes and drills the contact area (articulating surface) of the opposing teeth. Depending on the teeth involved, this articulating surface may be labial (front), lingual (back) or occlusal.

BRIEF DESCRIPTION OF THE DRAWINGS

FIG. 1 is a perspective illustration of a metal model of the prepared tooth and surrounding teeth.

FIG. 2 is a perspective illustration of a metal model of the counter, opposite from the prepared tooth.

FIG. 3 is an illustration of the set of wax pre-forms and the corresponding set of porcelain pre-forms, illustrating the selection of a wax pre-form to be placed over the prepared tooth.

FIG. 4 is a plaster impression in perspective. This plaster impression has been cast from the wax pre-form adjusted to be in place on the prepared tooth together with the teeth surrounding the wax pre-form. FIG. 4 shows the porcelain pre-form aligned to be placed into the plaster impression in the space made by the wax preform.

FIG. 5 illustrates the ultrasonic drillings of the gum line end (gingival contour and prepared tooth shape) of the porcelain pre-form in place on the FIG. 4 impression by use of the FIG. 1 model of the prepared tooth as an ultrasonic cutting tool.

FIG. 6 illustrates the ultrasonic drilling in the occlusal fitting step, with the porcelain pre-form in place on the FIG. 1 positive model of the prepared tooth by use of the FIG. 2 model of the counter as an ultrasonic cutting tool.

DESCRIPTION OF THE PREFERRED EMBODIMENT

With respect to terminology, the following will be used herein:
  a. Model. A model is a positive three-dimensional duplication of the item involved.
  b. Impression. An impression is a negative three-dimensional duplication of the item involved. A soft material is on a positive hard structure. After the soft material hardens over its hard impressed structure, and after it is separated.
  c. Gingival. Gingival refers to the gum line. Thus, the gingival side of a crown is the side closest to the gum line and is opposite from the incisal edge or occlusal surface.
  d. Incisal/Occlusal. This compound term refers to the biting edge of anterior teeth, or surfaces of posterior teeth. The incisal surface is the biting edge of the front teeth while the occlusal surface is the grinding and chewing surfaces of the bicuspids and molars. The incisal/occlusal side of a crown is opposite from its gingival side.
  e. Lingual. The lingual side of a tooth is the back surface facing into the mouth and thus is the surface adjacent to the tongue.
  f. Proximal. The proximal edges of a tooth are those vertical edges on sides closest to or touching adjacent teeth.
  g. Labial/Buccal. This compound term refers to the front surface of a tooth facing out of the mouth and thus is the surface closest to the lips or cheek.
  h. Restoration. This term is used herein to cover both crowns and prostheses such as fixed and removable bridges.

With reference to the FIGS., all of which illustrate the same embodiment of the invention, FIG. 1 illustrates a metal model 10 of the prepared tooth 12 and adjacent teeth 14. FIG. 2 illustrates a metal model 18 of the counter.

The metal models 10, 18 shown in FIGS. 1 and 2 may be made alternatively by (a) a technique wherein the prepared tooth and surrounding area, as well as the counter, are directly scanned and the data fed through a computer to operate a cutting tool that cuts into a soft metal to provide the models, or (b) a technique wherein an impression of the areas involved are scanned and a similar cutting operation performed, or (c) a technique in which the surfaces of a plastic impression of the areas involved are plated and the positive models formed therefrom. In this latter technique, a wax or alginate cast of the prepared tooth and area is taken. That impression is then plated with copper, nickel, silver or some soft metal that provides an accurate duplication of the surface involved. After the plating, the rest of the impression is filled with something like Mallot's metal or plastic. The wax or alginate is then removed and the result is a model that has on its outer surface the plating material of soft metal. The same technique is used to make the metal model 18 of the counter. At present, this latter technique is the preferred technique.

As illustrated in FIG. 3, this invention contemplates a set of wax pre-forms 20 for each type of teeth from incisor to molar and a corresponding set of solid porcelain pre-forms 22. Each wax pre-form 20 has a porcelain front surface 24, which surface 24 is known as the labial or buccal surface. In addition, each wax pre-form 20 has the incisal/occlusal surface covered in porcelain. Furthermore the pre-form 20 corresponding to the anterior (front) teeth have one-third of the lingual surface covered in porcelain. An indexing knob of porcelain on the lingual surface is identical in both wax pre-form 20 and solid porcelain pre-form 22. Only a portion of the front surface 24 is porcelain so that the wax pre-form 20 can be shaped at the gingival and proximal contacts by the dentist. From the set of wax pre-form 20 the dentist selects an appropriate pre-form to be fitted over the prepared tooth in the patient's mouth. The selection by the dentist is on the basis of size, shape, contours and the color of the porcelain front surface 24. The dentist then shapes and positions the wax pre-form as desired to provide a wax pre-form crown with a front surface 24 that is predominately porcelain. To do this the dentist may have to cut away part of the wax at the proximal and gingival surfaces. He also has to heat the wax to soften it for placement over the prepared tooth.

With this wax pre-form properly shaped and positioned on the patients prepared tooth, the dentist casts a plaster impression of the wax pre-form and surrounding teeth to provide the plaster impression 26 illustrated in FIG. 4. The plaster impression 26 when removed from the teeth will carry the wax pre-form 20 with it. The wax pre-form 20 is then removed from the plaster impression 26 to provide the impression 26 as shown.

The plaster impression 26 shown in FIG. 4 looks substantially like a plaster impression of a group of teeth in the mouth. However, the impression 26a left by the wax pre-form 20 is in part the result of manipulation by the dentist. This manipulation involves not merely the positioning of the wax preform 20 so that the porcelain facing is properly positioned and angled but also the heating and forming of the wax portions of the wax preform 20 to provide a proper fit between adjacent teeth. As a result the impression 26a left by the adjusted wax preform is likely to differ somewhat from the configuration of the corresponding porcelain stock preform 22. Thus, the dentist will normally have to scrape away a portion of the sides and perhaps even of the back of the plaster in the impression 26a left by the wax preform so that the porcelain preform 22 can be properly set in place. This procedure is a dental indexing procedure and involves setting the front surface of the porcelain preform 22 completely flush against the corresponding surface of the impression 26a made by the front surface 24 of the corresponding wax preform 20. It is these two surfaces (front surface of porcelain preform 22 and front surface of wax preform 20) which have to be indexed correctly so that the subsequent drilling steps will provide a properly fitting porcelain crown.

After the porcelain preform 22 has been indexed, it is removed from the plaster impression 26 shown in FIG. 4 and the plaster impression 26 is set in place in a tool holder. The metal model 10 of the prepared tooth and surrounding teeth is then placed in proper engagement with its own plaster impression 26 and the appropriate adjustments made in the supporting members so that proper alignment and engagement between the positive model 10 and the negative model 26 is made.

Once properly meshed, the combined metal model 10 and plaster impression 26 are held in a tool holder, by means of a vertical articulator such as The Fourier Dental Articulator (supplied by the Dentsply Company, Inc. of York, Pennsylvania). The metal model 10 is then lifted out of mesh with the plaster impression 26 while maintaining its alignment with the plaster impression 26 so that when the model 10 is brought down it will be brought back into proper engagement. The metal model 10 is then lifted vertically and the porcelain preform 22 placed in the impression at 26a.

In order to obtain appropriate engagement and alignment, it is important to have, as shown, a number of adjacent teeth 14 on either side of the prepared tooth 12 included as part of the metal model 10 and as part of the plaster impression 26. Three teeth 14 on either side of the prepared tooth 12 has been found adequate to provide the required meshing and consequent alignment.

A small procelain knob (not shown) on the lingual surface of both pre-forms 20 and 22 may be used to aid in the proper seating of the pre-form 22 in the cavity.

Then as shown in FIG. 5, with the porcelain pre-form 22 in place, the metal model 10 is brought down in continued alignment with the plaster impression 26. As the metal model 10 is brought down, ultrasonic energy is applied to the metal model 10 so that (with an appropriate pumice fed between model 10 and impression 26) the model 10 acts as a cutting or shaping surface to shape the porcelain pre-form 22. The prepared tooth model 12 effectively drills out the inside of the porcelain preform 22 and also serves to shape precisely, to a feather edge the contours and all internal and gingival surfaces of the porcelain pre-form 22. The proximal sides of the model adjacent teeth 14 serve to cut and shape the proximal sides of the porcelain pre-form 22. In this fashion, by means of ultrasonic energy, the model 10 becomes an ultrasonically powered tool which shapes and forms the porcelain pre-form 22 so that it can be properly placed on the patient's prepared tooth.

The result of the drilling step discussed above and illustrated in FIG. 5, is an intermediate product that still requires some further shaping. This further step, illustrated in FIG. 6, requires first aligning for proper bite the metal model 10 and counter model 18. This is done without the porcelain pre-form 22 in place. One way of aligning is by the usual wax bite method of transferring an occlusal relationship from the mouth to the models as in known in the profession when using an articulator device in making a crown.

After such alignment the two models 10 and 18 are moved apart while maintaining alignment and the intermediate product porcelain pre-form 22 is placed on the prepared tooth model 12. Then the counter model 18 is brought toward the model 10 with ultrasonic energy applied to the counter model 18. This ultrasonic energy causes the counter model to act as a cutting and shaping tool which then completes the cutting and shaping of the porcelain pre-form 22. As shown in the FIGS., the counter model 18 is much less complete than is the prepared tooth and surrounding area model 10. The reason for this is that the counter model 18 only has to be developed for enough of the opposing teeth to provide an appropriate bite for meshing and to shape the incisal/occlusal edge of the porcelain pre-form 22 together with whatever adjacent portions of the lingual (back) and/or labial/buccal (front) parts of the pre-form 22 are in the way of the counter teeth.

The above description is of an application of the invention to the preparation of a crown. The invention can be employed in the preparation of other prosthesis such as fixed and removable bridges.

In the claims the term tooth is used but it should be understood that there may be more than one prepared tooth (as in a bridge) and that the invention and the claims are not limited to the preparation of a crown and/or prosthesis for just one tooth.

In the claim the term wax is used to refer to the malleable material of the pre-form 20. It should be understood that other malleable materials may be used and are the equivalent of wax.

What is claimed is:

1. A set of paired preform teeth comprising:
    a first subset of preform teeth, each having a deformable body portion, a non-deformable front surface facing spaced from the proximal sides and gingival surface, and a non-deformable biting surface facing,
    a second subset of non-deformable preform teeth, each member of said second subset corresponding to one of said first subset, said correspondence including congruence between the front surface facing and biting surface facing of corresponding preforms from said first and second subsets,
    whereby, an impression model formed from a configuration including a member of said first subset will properly hold and align the corresponding member of said second subset for the purpose of drilling a socket in the member of said second subset for placement on a prepared tooth and whereby the adjustment of a member of said first subset on a prepared tooth will provide a configuration from which the impression for holding the corresponding member of said second subset can be made.

2. The set of paired preform teeth of claim 1 wherein: each member of said first subset includes a non-deformable back surface facing extending from the biting surface part way to the gingival surface and spaced from the proximal side.

3. The set of paired preform teeth of claim 1 wherein said facing of said first subset is porcelain and wherein said second subset is solid porcelain.

4. The set of paired preform teeth of claim 2 wherein said facing of said first subset is porcelain and wherein said second subset is solid porcelain.

5. The method of preparing a dental prosthesis from a preform comprising the steps of:
    forming a positive model of the patient's prepared tooth and surrounding area,
    shaping a deformable preform that has been placed on the prepared tooth, said deformable preform having a non-deformable partial facing,
    forming an impression model of the shaped preform in place on the prepared tooth, said impression including the area surrounding the prepared tooth,
    placing a rigid preform in said impression, said rigid preform having a facing congruent to said non-deformable partial facing of said deformable preform, and
    ultrasonically drilling the gum line side of said rigid preform in place in said impression using said positive model of the prepared tooth as the drilling tool to provide an intermediate product having a gingival contour congruent to the prepared tooth contour, whereby, the impression model will hold and align said rigid preform so that said positive model tool will form a socket in said rigid preform to permit fitting the rigid preform precisely over the prepared tooth in the patient's mouth.

6. The method of claim 5 further comprising the steps of:
   forming a positive model of the counter to the prepared tooth,
   placing said intermediate product on said positive model of the prepared tooth, and
   ultrasonically drilling the bite side of said intermediate product in place on said positive model of the prepared tooth using said positive model of the counter as the drilling tool to provide a prosthesis having an articulating surface that occludes with said counter.

7. The method of claim 5 wherein said rigid preform is porcelain.

8. The method of claim 6 wherein said rigid preform is porcelain.

9. The method of claim 5 wherein said rigid preform is a stock crown.

10. The method of claim 9 wherein said rigid preform is porcelain.

* * * * *